(12) United States Patent
Pierson et al.

(10) Patent No.: US 6,190,878 B1
(45) Date of Patent: Feb. 20, 2001

(54) DEVICE AND METHODS FOR DETERMINATION OF ANALYTE IN A SOLUTION

(75) Inventors: Mark W. Pierson, Saco; David Townsend, Scarborough, both of ME (US)

(73) Assignee: Idexx Laboratories, Inc., Westbrook, ME (US)

( * ) Notice: Under 35 U.S.C. 154(b), the term of this patent shall be extended for 0 days.

(21) Appl. No.: 09/179,922

(22) Filed: Oct. 27, 1998

Related U.S. Application Data

(60) Provisional application No. 60/063,635, filed on Oct. 27, 1997.

(51) Int. Cl.[7] .............................. C12Q 1/04; C12Q 1/00; C12Q 1/24
(52) U.S. Cl. ......................... 435/34; 435/283.1; 435/30; 435/4
(58) Field of Search .................. 435/34, 283.1, 435/4, 30

(56) References Cited

U.S. PATENT DOCUMENTS

| | | | |
|---|---|---|---|
| 3,960,658 | 6/1976 | Avakian et al. | 195/103.5 |
| 4,059,407 | 11/1977 | Hochstrasser | 23/253 |
| 4,197,287 | 4/1980 | Piasio et al. | 424/1 |
| 4,308,028 | 12/1981 | Elkins | 23/230 B |
| 4,925,789 | 5/1990 | Edberg | 435/38 |
| 5,492,933 | 2/1996 | Gray et al. | 514/648 |

FOREIGN PATENT DOCUMENTS

| | | |
|---|---|---|
| 0 042 755 A2 | 12/1981 | (EP) . |
| 0 459 093 A2 * | 3/1991 | (EP) . |
| 0 496 200 A2 * | 9/1992 | (EP) . |
| 0 709 678 A1 | 5/1996 | (EP) . |
| 2 188 418 | 9/1987 | (GB) . |
| 97/18455 * | 5/1997 | (WO) . |
| 9922017 * | 5/1999 | (WO) . |

OTHER PUBLICATIONS

Greenberg et al., *Standard Methods for the Examination of Water and Wastewater*, 8th ed. (1992) (Table of Contents Only) Month not available.

Recles et al., "Most Probable Number Techniques," *Compendium of Methods for the Microbiological Examination of Foods*, 3rd ed., pp. 105–120 (1992) Month not available.

\* cited by examiner

*Primary Examiner*—Louise N. Leary
(74) *Attorney, Agent, or Firm*—Mary S. Consalvi; Howrey Simon Arnold & White, LLP

(57) ABSTRACT

Method and assay devices for the detection of the presence or amount of biological material, analyte(s), or microorganism(s) in a sample. The method includes the steps of liquefying the sample (if necessary) and distributing the liquefied sample over the surface of the assay device. The device may comprise an incubation plate, a dip stick device, or other devices. The devices have at least one reagent provided within the devices. Some devices have a generally flat horizontal surface which is divided into a plurality of recessed wells. Others have one or more surfaces with reagent island(s) immobilized thereon. Each well or reagent island is adapted to hold an aliquot of liquid. The wells or reagent islands are sized and shaped, and formed of a suitable material, to hold the aliquot within the well or reagent island by surface tension. Any excess liquid from the liquefied sample is drained from the surface of the device. The method then involves incubating the assay device until the presence or amount of the biological material, analyte, or microorganism is determined.

25 Claims, 8 Drawing Sheets

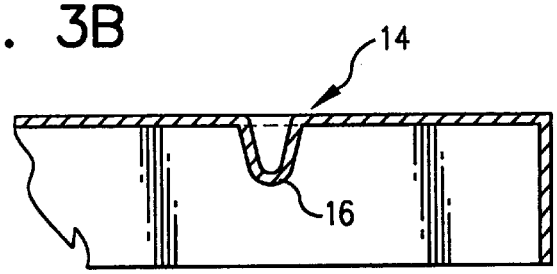
FIG. 3B
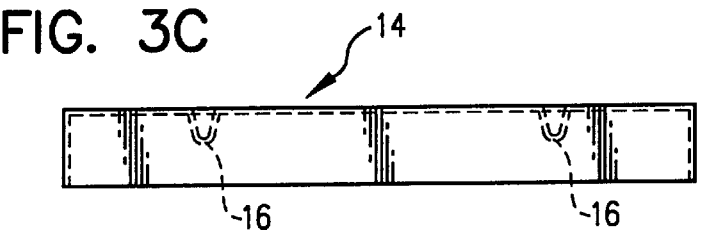
FIG. 3C
FIG. 4A
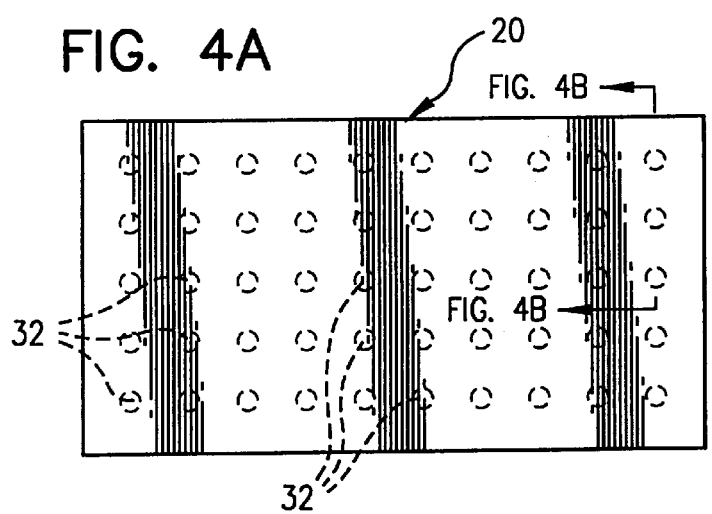
FIG. 4B
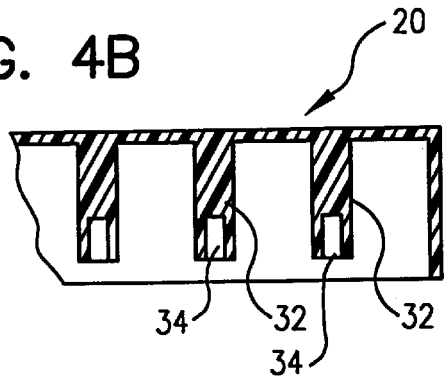
FIG. 4C
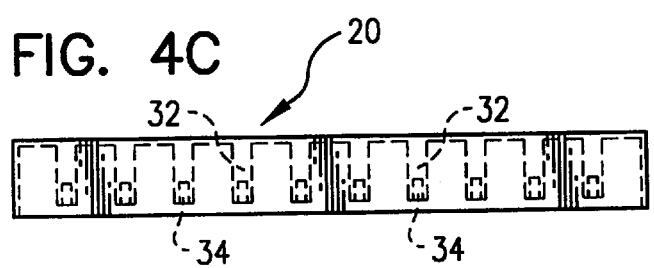

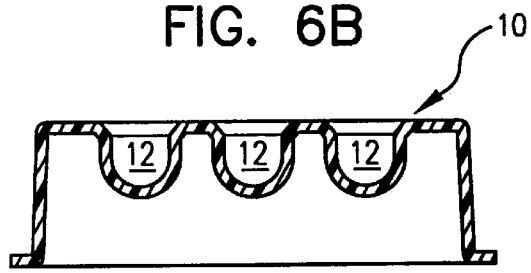
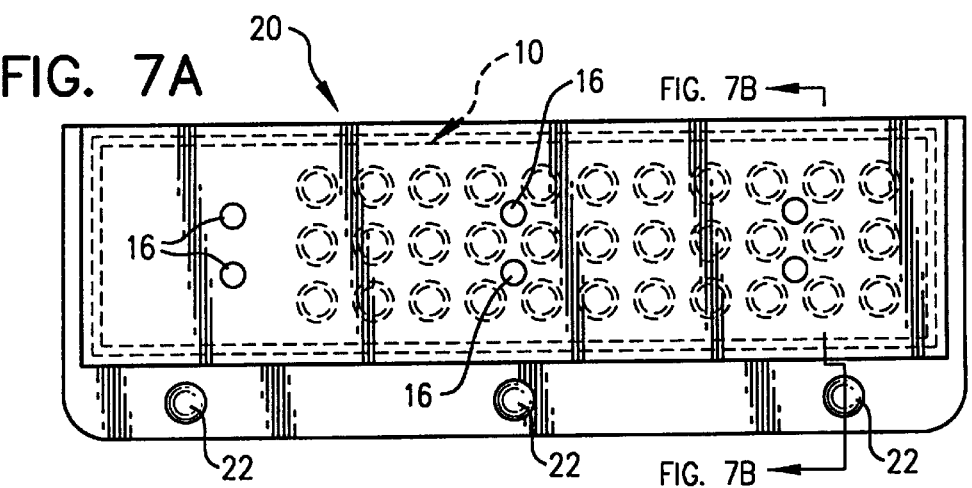
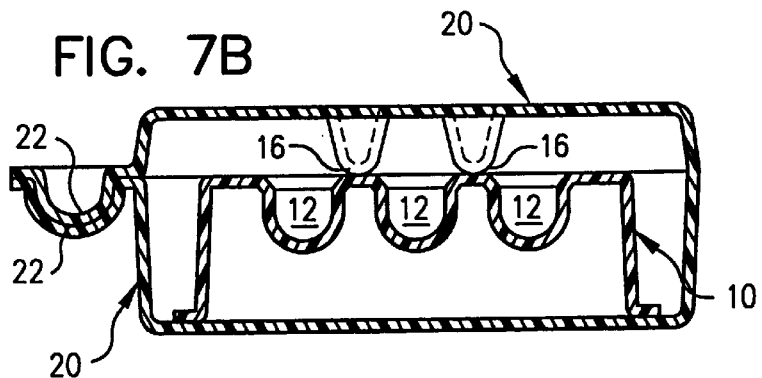
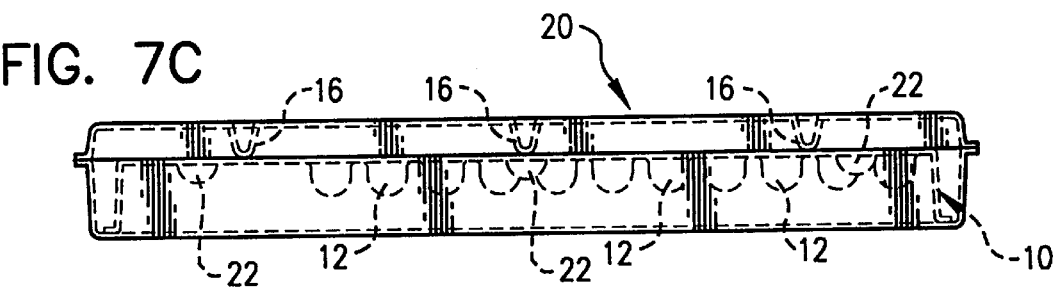

DEVICE AND METHODS FOR DETERMINATION OF ANALYTE IN A SOLUTION

RELATED APPLICATIONS

This application is a continuation-in-part of U.S. Provisional Application 60/063,635, entitled METHOD FOR QUANTITATION OF BIOLOGICAL MATERIAL IN A SAMPLE USING A REAGENT-CONTAINING INCUBATION PLATE, filed Oct. 27, 1997.

BACKGROUND OF THE INVENTION

This invention relates to the field of assay technology, and in particular embodiments, to devices and methods for quantification of analytes, e.g., biological material, in a sample.

Many industries need to detect and quantify the concentration and level of biological material or other analyte in a sample. For example, the determination of bacterial concentration in food and water is an essential part of food and water quality testing. EPA regulations require that no coliform such as *Escherichia coli* can be present in potable water. The "presence/absence" format of a testing medium, such as Colilert® chemical mixture (IDEXX Laboratories, ME) which is used as a testing medium for *Escherichia coli* and all coliform bacteria, is very useful in making this determination. Colilert® chemical mixture is based on the Defined Substrate Technology described in Edberg, "Method and Medium for use in Detecting Target Microbes In Situ in A Specimen Sample of A Possibly Contaminated Material," U.S. Pat. Nos. 4,925,789 and 5,492,933.

However, there are areas where the quantification, not just the detection, of bacterial concentration is important. Examples of such areas include waste water, incoming water in water purification systems, surface water, and food testing. For example, numerous restaurant chains will only accept raw ground beef or poultry that contains less than a certain concentration of bacterial contamination. Therefore, food processing plants must carry out the necessary microbiological tests to determine the bacterial concentration of these food items before they can be released to customers.

The classical methods of quantification of biological material are the standard plate count method or the multiple tube fermentation (MTF) method. A quantity of sample being tested for microbial contamination is first dispensed in a Petri dish. Then 15 ml of the appropriate media is poured over the sample. The Petri-dish is then swirled to mix the sample in the medium and the Petri-dish is left to solidify at room temperature for approximately 20 minutes. The medium is then incubated at a specific temperature for a specific time, and any resulting colonies are counted.

The multiple tube fermentation method is described in Recles et al., "Most Probable Number Techniques" published in "Compendium of Methods for the Microbiological Examination of Foods", 3rd ed. 1992, at pages 105–199, and in Greenberg et al., "Standard Methods For the Examination of Water and Wastewater" 8th ed. 1992). In this method, a volume of sample is dispensed into several tubes representing this dilution range. The tubes are then incubated at the appropriate temperature so that the bacteria in each tube are allowed to grow. After incubation at a specific temperature for a specific time, the number of positive tubes is counted. The most probable number can be determined from the formula described in Recles et al., supra.

Water testing is mostly done by membrane filtration, where a certain volume of water is passed through the membrane and the membrane is incubated in a medium for a certain period of time. After appropriate incubation, the colonies are counted.

In many industries there is also a need to qualitatively and/or quantitatively detect the presence of an analyte in a liquid solution. For example, the detection of inorganic ions may be important in a manufacturing process using a test solution.

Heretofore, the methods and devices generally relied upon for measuring an analyte in solution have either required removing all of an aliquot from the test solution or exposing a dip stick to a test solution. Although these methods and devices can detect an analyte in solution, they suffer from a number of disadvantages.

The dip stick-related methods are not quantitative. For example, in the general dip stick embodiments there is no capability for determining or quantifying the presence of an analyte in a unit volume of that solution. Instead, the dip stick is simply brought into contact with the test solution.

Other methods require a user to manually remove an aliquot from a test solution and transfer it to a separate device for detection or quantification of the analyte.

Therefore, despite the ability of these methods and devices to detect an analyte in solution, the methods and devices currently used have proven to have limited accuracy; and/or to be costly, complicated, time consuming; and/or to have a limited range of uses because of the particular assay technology.

Thus, there exists a need for a simple, accurate, and inexpensive method for the determination of an analyte in solution without the disadvantages known in the prior art. In particular, there is a need for devices and methods capable of providing a quantitative assay of an analyte in a particular volume of a solution.

SUMMARY OF INVENTION

The present invention provides devices and methods for detecting and enumerating the presence or absence of biological materials, analytes, and microorganisms in sample solutions.

In one aspect, the invention provides a sterile incubation plate for determining the presence or amount of a biological material in a test sample. The plate is generally described by a flat, horizontal surface containing recessed wells. Each well is adapted to hold an aliquot of liquid, and has a size and shape, and is made of a material, suitable for holding the liquid aliquot within the well by the forces of surface tension. At least one well contains at least one reagent for the detection of the biological material. No positive response is generated in the absence of the target biological material.

In a preferred embodiment, the reagent is deposited into the wells by corona treatment and drying. In another embodiment, the plate may also contain a lid. The well or wells may contain a plurality of reagents, and different wells may contain different reagents or different combinations of reagents, so that numerous assays can be conducted on a single plate. The plate is preferably constructed of plastic, however, it may be constructed of other hydrophobic material(s) which are suitable for conducting the assay. In a preferred embodiment, the plates of the present invention will be rectangular in shape, however, they may also be circular in shape, or of any shape. In a preferred embodiment the wells are about 0.15 inches in diameter. In another preferred embodiment, the wells of the plate hold a total of about 1-milliliter of solution. In another preferred embodiment, each well of the plate holds between 0.1 and 100 µl of liquid. The well or wells of the plate may be chamfered to aid in the removal of excess fluid. The plate may further comprise a handle portion so that the operator may manipulate the plate and conduct the assay without risk of contacting the test sample.

In another aspect, the invention provides a sterile incubation plate similar to the plate described above, and may be adapted with each of its embodiments, with the further feature that it comprises a lid which contains at least one protrusion(s) which fit(s) into the well(s). In this aspect, the reagent or combination of reagents is contained on the end of the protrusion(s) such that the reagent(s) will dissolve in the test sample upon closing or affixing the lid to the plate. In one embodiment, the protrusions may feature a cavity. The reagent(s) or combination of reagents will be dried onto the end of each protrusion or onto the surface of the cavity. The surface of the cavity can also be corona treated before depositing the reagent. In this aspect as well, a reagent(s) or combination(s) of reagents can be dried on, or the protrusion(s) corona treated, and a combination of reagents may be utilized among multiple protrusions so that multiple assays can be conducted on a single plate. The lower plate portion can be adapted to all of the embodiments with respect to the plate described above.

In another aspect, the invention describes a device for determining the presence or amount of an analyte(s) or microorganism(s) in a test solution. The device features a substantially hydrophobic support structure with at least one reagent island immobilized on the support structure which is capable of absorbing a predetermined volume of test solution. The device also comprises a means for determining the presence or amount of the analyte or microorganism, the means being positioned on or within the reagent island(s). This aspect of the invention may take the form of a plastic or polymer dip stick with one or more reagent island(s) immobilized on it. The reagent island may be made of any absorbent material, for example, cellulose.

The support structure may have multiple reagent islands immobilized on it. The means for determining the presence or amount of microorganisms or analyte(s) may comprise a powder which is incorporated onto or within the material from which the reagent island is prepared. The means may be a reagent or a combination of reagents which leads to a production of a detectable signal when target analyte(s) or microorganism(s) is present. The device may contain multiple reagent islands which can contain different reagents or combinations of reagents so that numerous assays can be conducted on a single device. In a preferred embodiment, the reagent islands are comprised of any absorbent material, for example, cellulose. The support structure can be constructed of plastic, polymer, or any suitable materials onto which a reagent island can be mounted and which will not interfere with the assay. In another embodiment, the device also comprises a container for holding the support structure before, during, and after conducting the assay. The container will typically comprise a test tube and may further comprise a cap for the test tube to further protect the device.

In another aspect, the invention provides an assay device for determining the presence or amount of an analyte(s) or microorganism(s) in a sample which comprises a substantially hydrophobic solid support structure with at least one discrete reagent island immobilized thereon which is capable of absorbing and holding a predetermined volume of test solution. Positioned on or within the reagent island is a means for determining the presence or absence of a target analyte or microorganism. This aspect of the device further comprises a container which is open at opposite ends. The container may typically take the form of a laboratory pipette. This aspect of the invention may comprise any of the various embodiments described with respect to the device described above. The reagent islands can also be arranged in zones such that each zone provides a separate assay. The reagent islands can be adapted to retain aliquots of liquid by surface tension or by absorption. The device may typically comprise an elongated strip. The reagent comprised in the reagent islands may be a growth medium or an indicator growth medium. The reagent may also be an enzyme or an enzyme substrate.

In another aspect, the invention provides an assay device for determining the presence or amount of an analyte(s) or microorganism(s) in a sample comprising a solid support structure with at least one reagent island immobilized thereon. Each reagent island is adapted to hold an aliquot of liquid and is of a size and shape and made of a material suitable to hold the aliquot within the reagent island. At least one of the reagent islands contains at least one reagent for the detection of the analyte(s) and/or microorganism(s) of interest. The device does not provide a positive response for the analyte(s) or microorganism(s) when the analyte(s) or microorganism(s) is not present in the test sample.

In a preferred embodiment, the reagent islands of the device may take up a preselected total volume. In one embodiment the device may comprise a combination of reagents located in separate reagent islands. In another embodiment, the reagent islands are arranged in zones, wherein each zone provides a separate assay so that multiple assays may be conducted on a single device. The reagent islands may be adapted to retain aliquots of liquid sample by surface tension or by absorption. The reagent islands may be adapted to each take up equal volumes of liquid. Or the reagent islands may exist in subsets of islands, wherein each subset consists of at least one island, and each subset takes up different volumes from the other subsets. The device may be constructed so that the reagent islands are immobilized on more than one surface. In different embodiments, the device may be a plate or an elongated strip. In a preferred embodiment, the support structure may be constructed of a hydrophobic material. In one embodiment, the at least one reagent may be a growth medium. In a specific embodiment, the growth medium may be a indicator growth medium. In various embodiments, the at least one reagent may be cells of at least one bacterial strain, an enzyme, or an enzyme substrate.

The invention also provides methods for detecting the presence or amount of biological material in a sample. In one aspect the method comprises the steps of 1) providing an incubation plate with at least one well which contains at least one reagent for detecting the biological material, the plate comprising a generally flat horizontal surface defining multiple recessed wells, each well being adapted to hold an aliquot of liquid, and being of a size and shape and constructed of a material suitable to hold the liquid aliquot within the well by surface tension and wherein at least one well contains at least one reagent for the detection of the biological material; 2) liquefying the test sample if necessary, and distributing the sample over the surface of the incubation plate; 3) draining off any excess liquid; and 4) incubating the plate until the presence or absence of the biological material in one or more wells is determined so that the amount of biological materials can be determined. The distributing step may comprise dipping the plate into the sample, or pouring, and may optionally include swirling or tipping.

This aspect of the invention can be adapted for all of the separate embodiments with respect to the plate devices discussed above.

In another aspect, the invention provides a method of detecting the presence or amount of a biological material in a sample, comprising the steps of 1) providing a sterile incubation plate with a lower portion which is a generally flat horizontal surface and contains multiple recessed wells adapted to hold an aliquot of liquid and being sized and shaped and formed of a material suitable to hold the liquid within the well by surface tension, and a lid with at least one protrusion containing at least one reagent for the detection of biological materials, wherein the protrusion fits into individual wells when the lid is closed on the lower plate portion; 2) liquefying the test sample if necessary, and distributing the sample over the surface of the incubation plate; 3) draining off any excess liquid from the plate; 4) closing the lid on the lower plate portion such that the reagent(s) on the at least one protrusion contacts aliquots of liquid in the wells, thereby allowing dissolution of the reagent(s); and 4) incubating the plate until the presence or absence of the biological material in one or more wells is determined so that the amount of biological materials can be determined.

This aspect of the invention can be adapted with all of the embodiments with respect to the methods discussed previously, and all of the embodiments with respect to the plate and lid device discussed previously.

In another aspect, the invention provides a method for making an incubation plate with at least one reagent, the method comprising the steps of 1) providing a plate with a generally flat horizontal surface with recessed wells which are sized and shaped and formed of a material suitable to hold aliquots of test sample within each well by surface tension; and 2) drying at least one reagent into the well(s).

In preferred embodiments at least one well may be corona treated prior to the drying step. In another embodiment, the corona treated portion may consist essentially of an inner surface of at least one well. In a preferred embodiment the reagent may be a cellular growth medium, or a bacterial growth medium. The plate may be made to suit all of the embodiments of the plates discussed previously.

In another aspect, the invention provides a method for making an incubation plate comprising the steps of 1) providing a sterile incubation plate with a lower portion which is a generally flat horizontal surface and contains recessed wells, each well adapted to hold an aliquot of liquid and being sized and shaped and formed of a material suitable to hold the aliquot by surface tension, and a lid with at least one protrusion which fits into the individual wells when the lid is closed on the lower plate portion; and 2) drying the reagent(s) onto at least one said protrusion. This aspect may contain all of the embodiments of the invention described previously with respect to the other methods and plate devices.

In another aspect, the invention provides a method of manufacturing a device useful for detecting an analyte(s) or microorganism(s) in a test solution, the method comprising the steps of 1) providing a material capable of absorbing a predetermined volume of liquid per amount of material; 2) preparing at least one reagent island from the material; 3) combining the material with a means for detecting the presence or amount of the analyte or microorganism; and 4) securing the reagent island to a substantially hydrophobic support structure.

In various embodiments, the preparing step may comprise preparing multiple reagent islands. In another embodiment, the reagent islands may be capable of absorbing a predetermined volume of solution.

In another aspect, the invention provides a method of detecting an analyte or microorganism in a test sample comprising the steps of 1) contacting the test sample with at least one reagent island capable of absorbing a predetermined volume of test solution and immobilized on a support structure, and which comprises a means for determining the presence or absence of an analyte or microorganism positioned on or within the reagent island(s); 2) separating the test sample from the reagent island(s) after the reagent island(s) has absorbed a predetermined amount of sample; 3) subjecting the reagent island(s) to reaction parameters which allow development of the reagent and generation of a sensible signal; and 4) determining the presence or amount of an analyte or microorganism.

In another aspect, the invention provides a method for detecting an analyte or microorganism in a test sample which comprises the steps of 1) selecting a test solution for the detection of the analyte or microorganism; 2) providing a device which comprises a substantially hydrophobic support structure and at least one reagent island(s) immobilized on the support structure, and which is capable of absorbing a predetermined volume of the test solution and comprises a means for determining the presence or amount of the analyte(s) or microorganism(s); 3) contacting the device with the test solution for a time sufficient to allow the reagent island(s) to absorb the predetermined volume; and 4) allowing the means for determining the presence or amount of an analyte(s) or microorganism(s) to determine the presence or amount of the analyte(s) or microorganism. In one embodiment, the contacting step may involve introducing the device into the test solution and removing it from the test solution. In another embodiment, the providing step may comprise providing a determining means which comprises a reagent which produces a sensible signal that signifies the presence or amount of an analyte(s) or microorganism(s). In another embodiment, the allowing step may comprise subjecting the device to reaction parameters sufficient to allow development of the reagent. Another step may be added to the method comprising observing the determining, or a step of determining the presence or amount of an analyte(s) or microorganism(s), or a step of determining the quantity of the analyte or microorganism.

BRIEF DESCRIPTION OF THE DRAWINGS

FIG. 3B is an enlarged, partial side view of the lid of FIG. 3A;

FIG. 3C is a side view of the lid of FIG. 3A;

FIG. 4A is a plan view of a second embodiment of a lid having a plurality of protrusions on the inner surface thereof;

FIG. 4B is an enlarged section of the lid of FIG. 4A taken at lines 4B—4B;

FIG. 4C is a side view of the lid of FIG. 4A;

FIG. 6B is a cross sectional view of FIG. 6A taken at lines 6B—6B;

FIG. 7A is a plan view of the embodiment of FIG. 6A having a lid placed thereon;

FIG. 7B is a cross sectional view taken at lines 7B—7B of FIG. 7A;

FIG. 7C is a side view of FIG. 7A;

DESCRIPTION OF THE PREFERRED EMBODIMENTS

Definitions

Figure 1A:
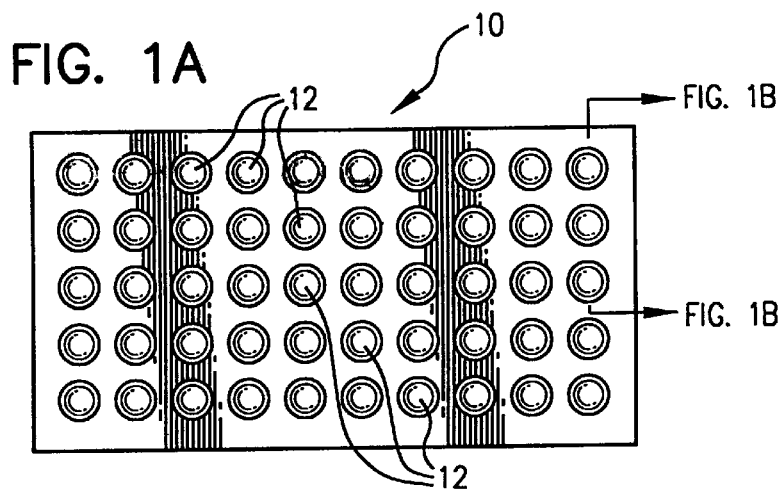
FIG. 1A is a plan view of a first embodiment of the device for the determination of analyte in solution of the present invention.

"Microorganism"—microorganisms means any microbe, including bacteria, fungi, or protists.

"Bacteria"—all organisms belonging to the Kingdom Monera.

"Biological Material"—any material derived from a biological organism.

"Target Organisms"—any "Microorganism", preferably but not limited to *E. coli*, yeast and/or mold.

"Cell"—any cell found in a plant, animal, bacteria, or any other living organism.

"Analyte"—any atom or molecule or ion which is involved in cellular metabolism in a living organism.

"Target Analyte"—any "Analyte", preferably but not limited to metabolites and/or enzymes.

"Proteinaceous Material"—proteins, peptides, enzymes, or amino acids.

"Hdrophobic"—having a sufficient degree of hydrophobicity to prevent "crosstalk" or bridging of liquids, such as samples or reagents, between adjacent incubation cells, wells or islands.

Structure

The present invention provides a simpler method for accurate quantification of the number of microorganisms in a sample, or for quantification of any other type of analyte, such as discrete particulate biological material within a sample. Such biological materials include fungi or other living organisms, as well as aggregates of proteins, such as enzymes, or even co-factors, using reaction mixtures well known to those in the art. The invention generally makes use of a novel article which is designed to take-up and hold a pre-selected volume of a liquid sample and to provide a reagent or reagents to such sample volume. In preferred embodiments, the pre-selected volume is divided into a plurality of sample aliquots. The plurality of sample aliquots may be all of the same volume or may be in sets of aliquots, where each set contains aliquots of different volumes.

The device used is generally in the form of a sterile incubation plate having a multitude of wells able to hold separate aliquots of liquid. The device is constructed to contain at least one reagent provided to the at least one well and preferably to a plurality or all of the individual wells. Because the plate, which can include a lid, contains the reagent or reagents, the reagent(s) is present in the plate prior to introduction of a sample. For example, such a reagent may be a specific growth medium for bacteria. The reagent(s) is provided prior to sample addition in a manner such that the reagent is not significantly washed or dissolved away during sample addition. The provision of the reagent or reagents within the plate eliminates the need for a tester to separately prepare the reagent and then add it to a sample or to the test plate. In addition, in many applications, the construction of the incubation plate is preferably arranged so that no pipetting is required, the plate is simply dipped into the sample, or an approximate quantity of the liquefied sample is poured onto the surface of the plate, and a designed volume of sample is retained within the wells. In this mode, the plate provides an auto-dispensing function.

Each well to which a reagent or reagents is provided may receive the same or different reagents. Thus, where a plurality of reagents is used, separate wells may receive different single reagents, different combinations of reagents, or combinations of these possibilities.

The phrase "at least one well is supplied with at least one reagent" means that one or more reagents are contained in the plate prior to sample addition in a manner so that the reagent or reagents will be present in a significant amount in at least one of the individual wells during incubation. Thus, the phrase distinguishes from situations where the user adds the reagent along with the sample or in such a manner that the reagent is substantially diluted or dissolved in the sample prior to draining off any excess sample liquid from the plate. In some embodiments, not every well will contain each reagent or may even contain no reagent. Thus, preferably the reagent or reagents are present in a manner such that a discrete quantity of reagent or reagents is supplied in or to each intended recipient well individually. While it is possible for a user to prepare a plate by depositing a reagent in the wells of a plate prior to sample addition, preferably the plate is provided to the user with the reagent(s) already deposited and preferably dried in place.

Generally, the wells are designed to form separate incubation chambers for each sample aliquot. The wells can be of the same size or of different sizes and shapes to increase counting range and/or simulate dilution effects.

Thus, in a first aspect, the invention features a sterile incubation plate having a generally flat horizontal surface. The surface defines a plurality of recessed wells (in preferred embodiments, at least 40, 60, 90 or even 200 recessed wells are provided) and each well is adapted to hold aliquots of liquid by surface tension. Any excess liquid from the liquid sample drains from the surface of the plate outside the wells due to the hydrophobicity of the material used to form the plate. The plate may be constructed of plastic or other hydrophobic material. In other embodiments, the plate may be generally circular in shape, or have any shape.

The plate is constructed to contain at least one reagent, e.g., a growth medium, and to provide that at least one reagent individually to at least one well. Thus, the reagent(s) is provided within the plate rather than being added separately. In general, the reagent or reagents are provided directly to individual wells. In other embodiments, different wells can contain different reagents or different combinations of reagents to provide a variety of applications. For example, the provision of different reagents or different combinations of reagents to different wells can provide a plurality of different assays on a single plate. The reagent(s) is provided in such a manner that it is not appreciably washed away during the aliquoting or auto-aliquoting process (as described below).

In other preferred embodiments, a lid is also provided to prevent contamination of liquid within the wells; and the plate is provided in a sterile form so that no positive aliquots are noted unless at least one biological material particle is present in the sample. In embodiments in which a lid is present, the lid is regarded as part of the incubation plate, whether attached or separate from the plate portion containing the wells. In this context, the lid is the "lid portion", and the plate portion containing the wells is the "lower plate portion". The lid can be a top cover, but can also be constructed as a container, such as a clamshell arrangement, so that the plate portion containing the wells can be fully contained within the lid/container. In another preferred embodiment, the lid is designed as a rectangular tube, such that the plate portion is inserted into the open end of the tube; generally an enlarged portion of the plate will close the open end of the tube-shaped lid.

In a preferred embodiment, the reagent is coated into individual wells in a manner so that the reagent will not be appreciably washed or dissolved out of the well during the process of distributing the sample into the wells. As an example, the inner surface of the wells can be corona treated so that the reagent will tightly adhere to the plate when dried and will therefore dissolve only slowly when contacted with the liquid sample. Additional agents can be added to the medium or coated on the medium in the wells to further control the dissolution rate.

In other preferred embodiments, the plate includes a lid which has a structure designed and adapted to deliver the reagent(s) to the individual well(s). For example, the lid can be constructed with a projection or protuberance which holds the reagent, and preferably a plurality of such projections or protuberances, such as a projection for each well. The lid may be attached to the lower portion of the plate or may be separate. When the lid is closed, or placed onto the lower portion of the plate after aliquoting of the sample, the reagent will contact the liquid sample in the well and will then dissolve into the liquid sample. The reagent may be coated onto the projection, such as by using corona treatment of the surface of the projection to adhere the reagent to the projection. The reagent may also be dried onto the protrusion or protrusions of the lid. The projection may also have a cavity to hold the reagent, the surface of which may be treated to improve adhesion of the reagent. Different reagents, or different combinations of reagents may be coated onto each of the projections.

In yet other embodiments, the plate has a reagent delivery portion. The reagent delivery portion is constructed to hold a selected quantity or quantities of one or more reagents and to deliver that reagent(s) individually to one or more wells. For example, the reagent delivery portion can be a frame attached to the underside of a lid portion with rings or cylinders which hold the reagent or reagents. When the lid is closed following sample distribution, the reagent or reagents will contact the individual sample aliquots and disperse in the liquid. Other configurations can also be designed.

Figure 2A:
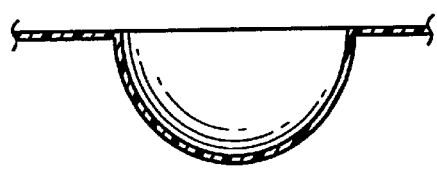
FIG. 2A is an enlarged view of FIG. 1B showing a well without a chamfer.
Figure 2B:
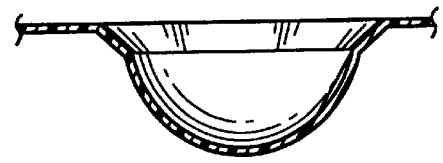
FIG. 2B is an enlarged view of FIG. 1B showing a well with a chamfer.

The generally flat horizontal surface is designed to allow the liquid to be aliquoted readily between the wells and then excess liquid to be drained from the plate while retaining a liquid sample aliquot within each of the wells. Those in the art will recognize that the depth and shape of the wells, as well as the material used to make the wells and the plate, are chosen such that surface tension can be used to hold the aliquots against gravity within each well, dependent on the type of the liquid used in the liquefied sample; those skilled in the art will understand the factors for selecting plate materials and well sizes appropriate for the various liquids. Preferably the sample is an aqueous solution, more preferably a dilute aqueous solution or suspension. In a preferred embodiment, the well has a diameter of about 0.15 or 0.16 inches. Preferably a well holds between 5 and 100 $\mu$l. Also in preferred embodiments, the well may have a shape designed to enhance retention of a sample aliquot, and/or retention of reagent within the well. An example of such an alternate well shape is a generally circular well with ribs projecting toward the center of the well, but other designs can also be used. In a preferred embodiment the wells are chamfered to allow liquid that is above the horizontal plane to be poured off easily (see FIG. 2B). The dimensions of the wells and the number of wells on a plate can be selected so that a particular total volume is retained on a plate. Preferably a plate retains a total of between about 0.1 and 10 ml., more preferably about 0.5, 1, or 2 ml., within the wells.

The incubation plate may be formed of any desired material, but in particular it is desirable that a plastic be used which allows separate aliquots of the liquefied sample to be held by surface tension within each well without cross contamination of the wells. Preferably, the material is hydrophobic. The surface can be untreated or treated chemically or physically to enhance retention of liquid within the wells, even when the plate is inverted or tipped at any angle from the horizontal. The plate may also be treated to enhance adhesion of a reagent or reagents within a well or on another desired surface of the plate, for example corona treated. Generally, the reagent will be dried onto the plate surface.

In yet other preferred embodiments, the incubation plate is clear or colored, for example, white or yellow (to enhance the appearance of color (e.g., blue)) within the incubation plate), and the plate has rectangular dimensions of about 1.5 by 2.5 inches or 1 by 4 inches, or for circular plates, a diameter of about 3 or 5 inches .

In related aspects, the invention features methods for detection of a biological material in a sample using an incubation plate having at least one reagent as described above. The methods include the steps of liquefying the sample (if necessary) and distributing the liquefied sample over the surface of an incubation plate as described for the above aspect, preferably by dipping the plate into the sample. In an alternative embodiment, the sample is poured into the plate and the plate is tipped or swirled as needed to distribute the sample; in this embodiment, the well-containing area of the plate is surrounded by a wall which retains the sample on the plate during sample distribution. As described above, each well is adapted to hold an aliquot of liquid and is sized and shaped, and formed of a suitable material, to hold the aliquot within the well by surface tension. The aliquots of liquid enter the individual wells without being applied individually, and therefore the method incorporates automatic aliquoting (or auto-aliquoting). Any excess liquid from the liquefied sample drains from the surface of the plate outside the wells due to the hydrophobicity of the material used to form the plate.

In one method the plate has at least one reagent in at least one well prior to sample addition, so that following autoaliqouting of the liquid sample into the wells, the reagent or reagents dissolve into the liquid. In a related method, the reagent or reagents are contained in the lid, such as on or in protrusions in the lid which project into wells when the lid is closed on the lower plate portion. Thus, when the lid is closed, the reagent(s) contacts the liquid aliquot in the individual well or wells, and then disperses or dissolves in the liquid.

In the context of this invention, the term "dipping" refers to a brief immersion of at least a portion of an incubation plate in a liquid. Preferably the period of immersion is less than about 3 seconds, more preferably less than about 2 seconds, and still more preferably less than about 1 second.

As described, the plate is constructed to contain at least one reagent, such as a growth medium, and preferably all the reagents needed for the particular assay where the reagent is in the plate prior to distribution of the sample. In other embodiments, different wells can contain different reagents to provide a variety of applications, for example, to provide a plurality of different assays on a single plate. The reagent(s) is provided in such a manner that it is not appreciably washed away during the auto-aliquoting process. Any needed reagents not provided directly in the device can be provided in the sample or directly into the plate at the time of use. The method then involves incubating that incubation plate until the presence or absence of the biological material is determined.

Also in preferred embodiments, the plate is provided with a handle portion by which the user can grasp the plate while avoiding contact with the sample application portion of the plate. For applications where the sample is distributed over the surface of the plate by dipping the plate into the sample, at least a portion of the handle is not dipped into the sample, thus aiding in preventing contamination of the plate and/or the sample by contact with the user's hand.

The shape of the incubation plate is not critical, but in preferred embodiments is a generally rectangular shape. Another example is a generally circular shape (such as that of a Petri dish). Indeed, the incubation plate can be used to take the place of a Petri dish. Specifically, the method of this invention can be used to replace those existing tests that are generally run on Petri dishes to score the number of microbial colonies. Since discrete aliquots of the sample are provided in the plate, one of ordinary skill in the art need only score the number of positive wells in the plate to define the quantity of biological material within the original sample, as with the MPN test discussed above. In preferred embodiments, the incubation plates of these methods are constructed of plastic, or other hydrophobic materials.

As noted above, the biological material that can be detected is any material that forms a discrete particle, such as a microorganism, which may be quantified by determining the presence or absence of such a biological material within each well of the incubation plate. The sample may be any biological sample or environmental sample such as waste water, food, a surface swab, or swabs from other surfaces, such as a throat, or other samples well known to those in the art. This sample may be a liquid sample, or may be dissolved in a liquid to form the liquefied sample. Thus, the term "liquefying" refers to providing the sample in a liquid that can be rapidly aliquoted within the incubation plate. The liquefied sample may remain as a liquid or may be solidified, e.g., gelled, in the wells after excess liquid is removed.

This invention provides an extremely useful device and method which allows unskilled personnel to rapidly determine the quantity of biological material within a sample. Since the sample is readily liquefied by people without significant training in microbiology, and the materials for any specific tests can be provided by the manufacturer, such people can readily perform the tests with accuracy. The incubation plate is generally provided in the sterile form so that no inappropriate detection of biological material can occur.

While it is known to provide plastic containers which can hold liquid within a plurality of recesses, this device and method provides an automatic aliquoting (or auto-aliquoting) method in which the steps to be performed by the tester are reduced and simplified by removing the requirement for manual addition of a reagent and preferably also eliminating the need for pipetting a sample or other liquid onto the plate. This is an improvement over the existing products used to detect and quantify microorganisms because the potential for contamination of the reagent or errors in dilution are reduced.

The present device can be used particularly in food analysis and in testing of clinical samples. The separation of the wells of the present device prevents crosstalk or contamination between each aliquot. Because of this, many of the tests can be performed by observing fluorescence (which is not readily performed in an agar-containing Petri dish). The device is particularly useful when there is a large quantity of microorganisms present in a sample, such as more than one organism per one ml or per ten ml.

Other features and advantages of the invention will be apparent from the following description of the preferred embodiments thereof, and from the claims.

Figure 3A:
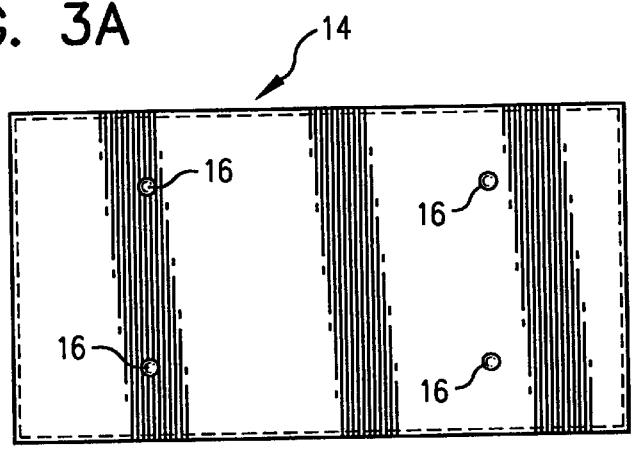
FIG. 3A is a plan view of a lid for the device of the first embodiment of FIG. 1A.
Figure 3D:
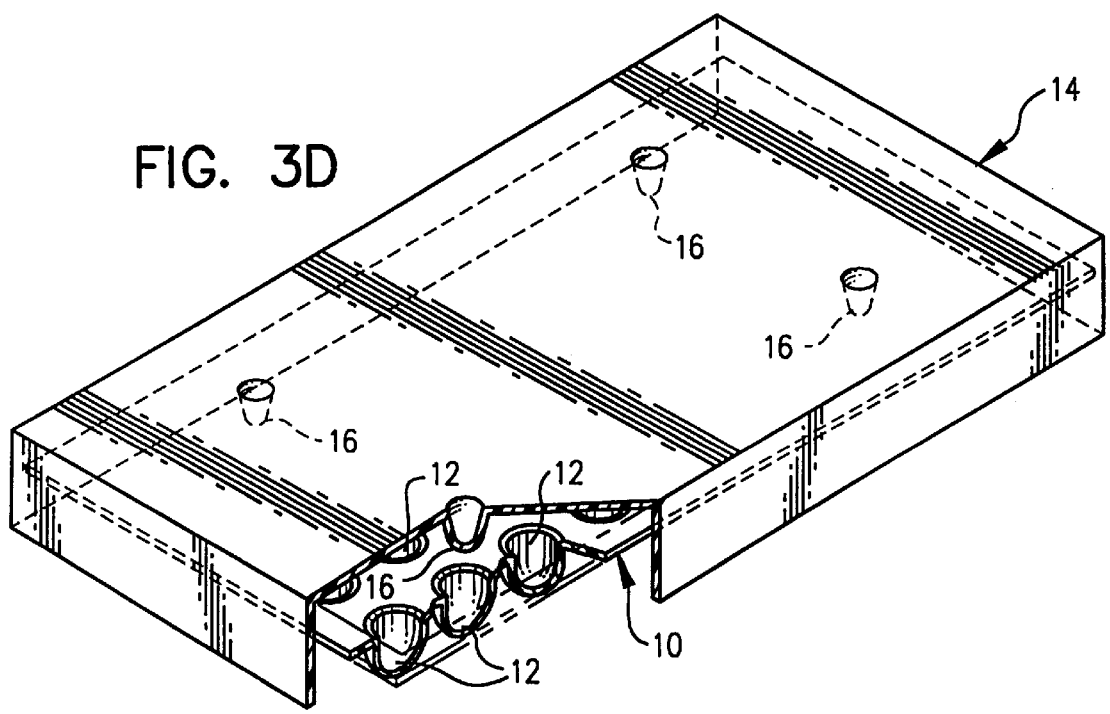
FIG. 3D is a perspective view, partially exposed of the lid of FIG. 3A placed over the device of FIG. 1A.
Figure 4D:
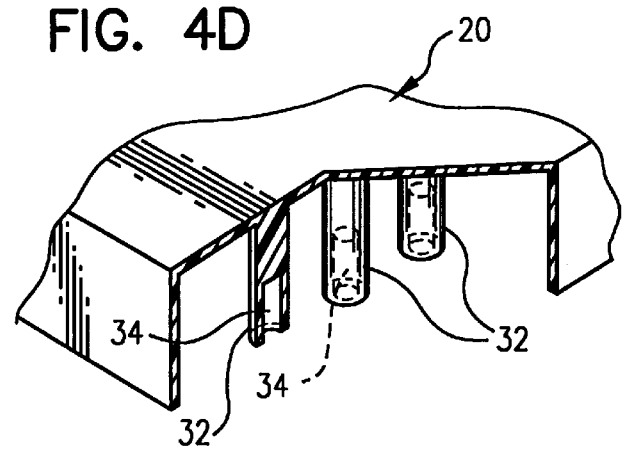
FIG. 4D is a partially exposed, enlarged perspective view of a portion of the lid of FIG. 4A showing the protrusions thereof.
Figure 5D:
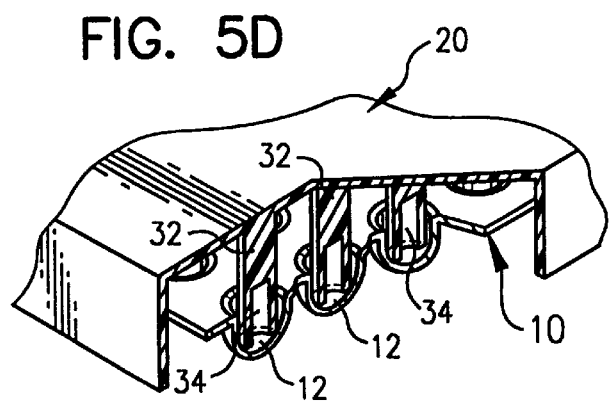
FIG. 5D is a view of the lid placed onto the lower portion of the plate.
Figure 5A:
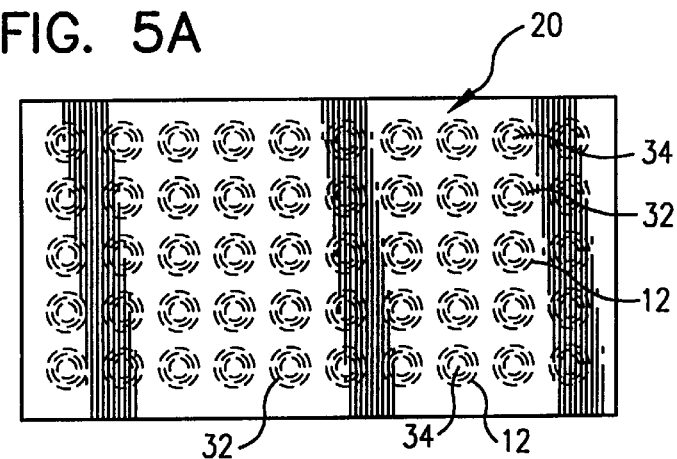
FIG. 5A is a plan view showing the lid of FIG. 4A placed on the device of FIG. 1A.
Figure 5B:
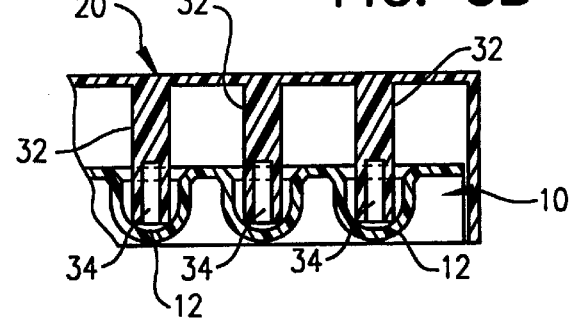
FIG. 5B is an enlarged, exposed view of FIG. 5A.
Figure 5C:
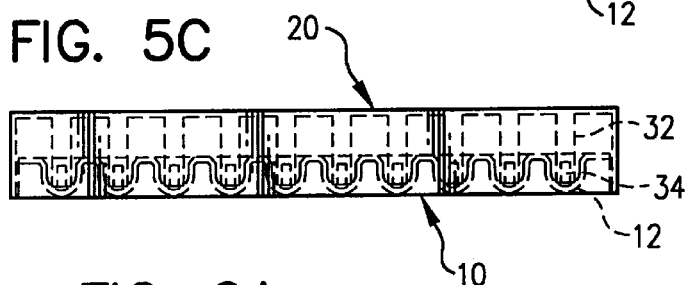
FIG. 5C is a side view of FIG. 5A.

Referring to FIGS. 1A–1D, there is shown an incubation plate 10 having a plurality of wells 12 each having a diameter of about 0.16 inches. The incubation plate 10 has rectangular dimensions of about 2.7×1.4 inches. The incubation plate is made of formed plastic. Wells 12 are spaced apart sufficiently to prevent crosstalk between the wells. These wells may have a chamfer (FIG. 2B) if desired to prevent liquid remaining at the upper edge of the well. The inner surfaces of the wells can be corona treated and a reagent, such as a growth medium, can be dried onto those surfaces. The reagent can be either a single reagent or a combination of reagents. Those in the art will recognize that incubation plate 10 can be readily formed by standard procedures and manufactured with or without perimeter wall, and with or without a lid 14 (FIGS. 3A–3C). This lid is provided with dimples 16 to prevent contact of the lid with plate 10.

Referring to FIGS. 4A–4D and 5A–5D, a rectangular incubation plate 10 is shown with a corresponding lid 20. The lid is constructed with a set of projections or protrusions 32 which project into the wells 12 of the plate when the lid is closed on the plate. The reagent may be applied to the ends of these protrusions so that when the lid is placed on the plate, the protrusions project into the well and the reagent dissolves in the test sample. The lid can be separate from the lower plate or can be formed as an integral part. For example, the lid portion can be attached to the lower plate portion with a thin plastic "hinge portion", which will allow the lid to be closed onto the lower plate portion. In this exemplary embodiment, each of the lid protrusions has a cavity 34 in the tip, into which is deposited a reagent. The inner surface of the cavity can be corona treated to enhance adhesion of the reagent, and the reagent can then be dried onto the corona treated region. In use, the sample would be auto-aliquoted into the wells, then closure of the lid would bring the tips of the protrusions into contact with the liquid in the wells. This contact will result in dissolution of the reagent contained in the cavities in the tips of the protrusions into each of the sample aliquots. In the case where the reagent is a bacterial growth medium and the sample contains bacteria able to grow in that medium, bacterial growth can then occur in the wells in which there are viable bacteria.

Figure 1B:
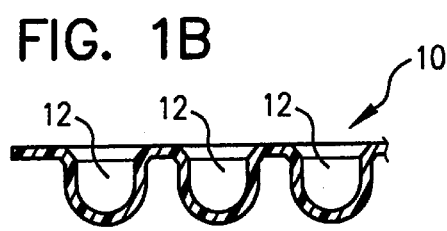
FIG. 1B is an enlarged cross section of FIG. 1A taken at lines 1B—1B.
Figure 1C:
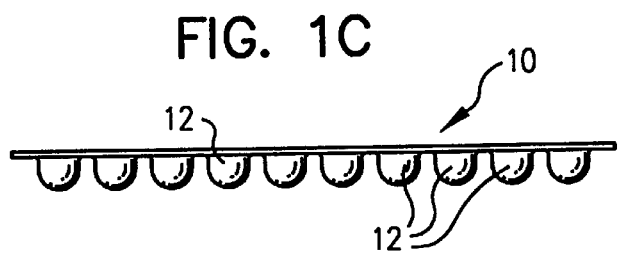
FIG. 1C is a side view of the first embodiment of the present invention of FIG. 1A.
Figure 6A:
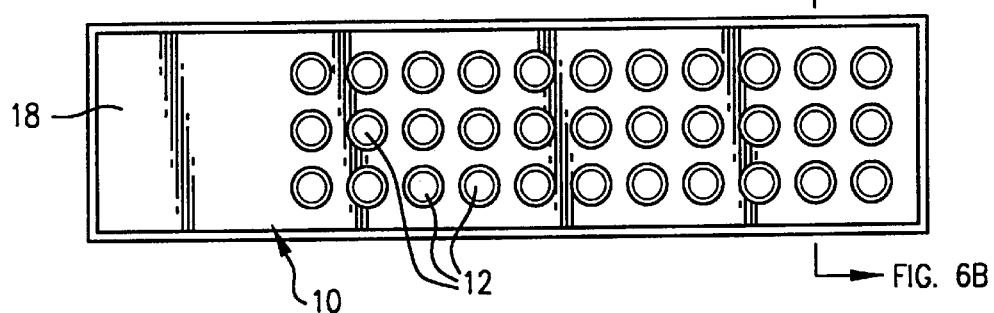
FIG. 6A is a plan view of a second embodiment of the device of the present invention having a handle.
Figure 6C:
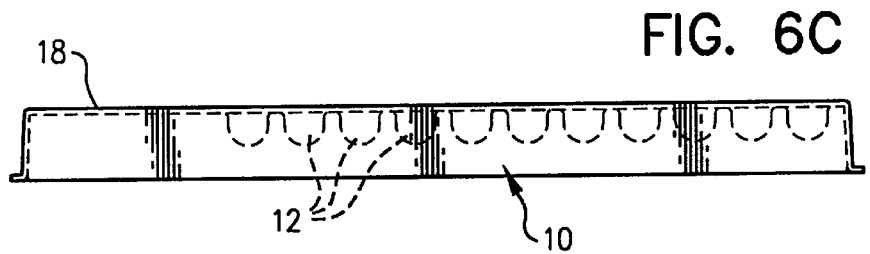
FIG. 6C is a side view of the second embodiment of the device of FIG. 6A.

Referring to FIGS. 6A–6C, a rectangular incubation plate 10 is shown which is similar in construction to the plate of FIGS. 1A–1C, except in having a handle portion 18. A user can grasp the handle portion, thereby avoiding possible accidental contact with the sample application area of the plate. In addition, in applications in which the plate is dipped into a liquid sample, by grasping the handle portion, contact of the user's fingers or a holding device with the bulk sample can be avoided, thereby reducing the chance of accidental contamination of the sample.

The plate 10 of FIGS. 6A–6C is also shown in FIGS. 7A–7C, together with a lid 20. This exemplary lid is formed to fully enclose the plate, and is thereby able to prevent contamination of the underside of a dipped plate, and to prevent contamination of bench surfaces or other objects with liquefied sample from the underside of a dipped plate. Thus, in use, the well-containing portion of the plate is dipped into a liquefied sample, excess liquid is drained from the plate, and the plate is inserted into the lid/container for incubation. The lid/container 20 can be held closed using friction-fit matching depressions 22 in the upper and lower portions of the lid. The wells of the plate may be chamfered.

Coating of Plate Surfaces with Reagent

A variety of different methods can be used for providing a reagent or reagents within an incubation plate. For example, a reagent could be provided so that the reagent would be readily and quickly dissolved on contact with a buffer or solution, preferably aqueous solution. In such an embodiment, the quantity of liquid added should be controlled so that the resulting concentration of reagent distributed into the wells would be appropriate. Thus, in this case, the reagent could be placed inside the incubation plate in any manner and location which would retain the reagent during handling but would allow rapid dissolution on addition of the liquid.

In this invention, however, the reagent is provided in a manner and/or location in the plate so that it is not necessary to measure the volume of liquefied sample with which the plate is contacted in order to obtain an appropriate concentration of reagent within the sample aliquots retained in the wells. This is achieved by providing a discrete quantity of the reagent directly to each well in which the presence of the reagent is desired. Such discrete quantities can be provided in a variety of ways, including the particular embodiments described herein. These embodiments either use reagent adhered to the well surface in such a manner that the amount of reagent dissolving during the auto-aliquoting process is negligible, or provide reagent in a location so that it does not come into contact with liquid until after the auto-aliquoting process is complete.

For example, the inner surface of one or more wells can be corona treated and reagent dried onto the treated surface, such as from a highly concentrated reagent solution. Reagent deposited in this manner will dissolve slowly, so that the amount lost during the auto-aliquoting process will be negligible. The majority of the reagent will then dissolve during the initial part of the incubation period. The dissolution rate can also be controlled by selection of the media components.

In another example, reagent can be deposited onto protrusions from the surface of the plate lid. The protrusions are positioned so that the tips of the protrusions will project into individual wells when the lid is closed on the plate. Reagent can be deposited on the outer surface of protrusions, but preferably is deposited into cavities in the tip of the protrusions. The reagent can be deposited in any manner which will result in the reagent being substantially retained in position during pre-use handling of the plate. Thus, for example, the reagent can be retained by physical barrier means, but is preferably adhered to the surface of the protrusion and/or the surface of a cavity in the tip of the protrusion, such as by a process involving corona treatment and drying of the reagent onto the treated surface.

Corona Treatment and Reagent Deposition

Typical plastics are made up of long chains of linked subunits, for example, polyethylene is composed of long chains of ethylene subunits. In general, aqueous solutions and the solutes in aqueous solutions are not attracted to interior chain subunits and therefore will not bind effectively to such locations. In contrast, there is often much greater affinity between such solutes and chain ends, particularly where the chain end has a relatively polar character. As understood by those skilled in the art, corona treatment is a method which increases the hydrophilicity of a treated plastic surface. The corona treatment process generally entails passing the plastic through an electric arc. The energy imparted by the electric arc introduces a significant number of chain breaks, thereby increasing the number of relatively hydrophilic ends available for interaction. In addition, the electric arc also generates ozone, which, as a strong oxidizing agent generates still additional chain breaks and polar side groups by oxidizing bonds within the polymer chains.

As indicated, this treatment process increases the binding of polar compounds, such as aqueous solution components. Therefore, for the use of corona treatment in preparing plates of this invention, following the corona treatment of the well surfaces, a concentrated solution of reagent is dispensed into the wells. As the Corona treated surfaces are now wettable (e.g., hydrophilic) the liquid reagent forms a uniform coating over the surface of the well. The plate is then dried, generally in a drying oven, driving off the liquid water and leaving a hard, coating of solid reagent in the wells.

As noted above, different reagents can be delivered to different wells, and/or some wells may receive no reagent. Wells receiving no reagent would also usually not be corona treated. Other methods known in the art can also be used to increase the adhesion of reagent to the appropriate plate surfaces.

Use

In use, a test sample can be liquefied or diluted with an appropriate sterile buffer or saline solution. A quantity of the liquefied sample can then be distributed over the surface of the plate. In a preferred mode of use, the liquefied sample is expected to contain or is diluted to contain about 1–40 units of the biological material to be quantified, e.g., viable bacterial cells. An incubation plate 10 of for example FIGS. 1A–1C is dipped into the liquid sample sufficiently to fill the wells, withdrawn, and allowed to drain briefly by holding at about 90 degrees to the horizontal. In this use mode, the plate provides both an auto-aliquoting function and an auto-dispensing function. Alternatively, in the case of a plate having a perimeter wall, an excess of the liquefied sample is placed in the incubation plate 10 and that liquid swirled within incubation plate 10 to distribute the inoculated liquid to each of wells 12. Incubation plate 10 is then held at an angle of approximately 90 degrees to allow excess liquid to drain from the plate. As shown in FIGS. 3A–3C, a lid 14 may then be placed on the incubation plate and that plate held in an incubator for the appropriate length of time, for example 18–48 hours. After that length of time, the presence or absence of a positive result can be scored in each well 12 of the plate.

Example 1: Use of Incubation Plate For Bulk Testing

For total plate count, a plate as described above is used for the detection and quantification of the total bacterial concentration of food. It can be based on a multiple enzyme technology which correlates enzyme activity to the presence of viable bacteria in food. It utilizes multiple enzyme substrates that produce a blue fluorescent color when metabolized by bacteria. The multiple enzyme reagent is coated on interior surfaces of wells of the plate. When a liquefied prepared food sample is distributed into the wells of a plate as described herein, the total viable bacterial concentration of that food product can be determined after 24 hours of incubation. The actual medium used herein is not critical to the invention, but is provided only for illustrative purposes.

Storage and Disposal

Unused test plates are stored at room temperature (4° to 25° C.) away from the light. After use, the incubation plate device will contain viable bacteria which must be handled and discarded appropriately.

Test Procedure—Dip Method Sample Application

1. Obtain a sample by removing an appropriate quantity of a bulk material to be tested. If needed the sample is liquefied or diluted in a sufficient volume to allow a plate to be dipped into the sample.

2. Grasp an incubation plate without contacting the sample application surface (preferably grasp the plate by the handle portion if the plate includes such a portion). Dip the bottom portion of an opened incubation plate into the sample, withdraw the plate immediately, and hold at approximately 90 degrees to the horizontal to allow excess liquid to drain from the plate. Preferably the excess liquid is allowed to drain into a waste receptacle rather than being allowed to drain back into the sample container in order to reduce the possible deposition of reagent into the sample container. Make sure that all liquid "cross bridges" between wells are removed by gently tapping the plate. Dispose of excess liquid appropriately.

3. Place the lid back on the plate (or close an attached lid).

4. Place the plate in an incubator for 24 hours. Plates can be inverted if desired.

5. Count the number of fluorescent wells after 24 hours by placing a 6 watt 365 nm UV light within five inches of the plate. Do not read plate before 24 hours. Results are stable to 48 hours.

6. Compare the number of fluorescent wells to an MPN chart to determine the most probable number of bacterial present in the plate.

Example 2: Use of Incubation Plate for Unit Dose Testing

The plate containing media described in Example 1 are used for this test.

Test Procedure

1. Add 10 ml of sterile buffer (or saline) to a tube. If greater than 0.1 ml of food sample is to be inoculated into the test, reduce the volume of sterile buffer appropriately to achieve a final volume of 10 ml in the tube.

2. Inoculate the buffer with the food sample being tested.

3. Shake the tube several times to completely mix buffer and inoculated food sample.

4. If the tube is of sufficient size, dip the plate into the sample or alternatively pour the buffer/sample suspension over the sample application surface of an incubation plate as appropriate, taking care that all the wells are filled. After sample application, immediately hold the plate at approximately 90 degrees to the horizontal to allow excess liquid to drain from the plate. Preferably the excess liquid is allowed to drain into a waste receptacle. Make sure that all liquid "cross bridges" between wells are removed by gently tapping the plate. Dispose of excess liquid appropriately.

5. Place the lid back on the plate (or close an attached lid).

6. Place the plate in an incubator for 24 hours. Plates can be inverted if desired.

7. Count the number of fluorescent wells after 24 hours by placing a 6 watt 365 nm UV light within five inches of the plate. Do not read plate before 24 hours. Results are stable to 48 hours.

8. Compare the number of fluorescent wells to an MPN chart to determine the most probable number of bacterial present in the plate.

The patent documents and other references cited herein are each incorporated by reference to the same extent as if each had been separately incorporated by reference in its entirety.

Dip Stick Testing Device For Microorganism Detection and Enumeration

Next referring to FIGS. 8–13, the concept is to use small individual absorbent materials which contain lyophilized or "dip-dried" reagent in a setting that allows automatic sample distribution and target microorganism enumeration.

A number of reagent-containing absorbent (hydrophilic) materials ("reagent islands") are immobilized onto a support structure made of a hydrophobic material to form individual reagent islands. The reagent islands may be embedded in the support structure, for example. However, this should not be construed as limiting as any form of securing the reagent island to the support structure may be used as long as it does not interfere with the assay. The liquid absorbing rate of each reagent island in this embodiment is the same because the reagent islands are made of the same material and have the same size. Further configuration can be made so there are two or more groups of reagent islands in different sizes to form a setting that can be used to achieve higher microorganism quantification without serial dilution based on the principles of the Most Probable Number (MPN) method.

In a preferred embodiment, the reagent is one developed to test for the presence of target microorganisms in a sample using, but not limited to, defined substrate technology (DST) and/or Multiple Enzyme Technology (MET). A positive detection of target microorganisms in such reagents will cause a color change of the reagent and/or cause the emission of a fluorescent signal from the reagent when viewing under a long-wave UV lamp. Examples of such reagents are Colilert®, Enterolert™, Simplate TPC™, and Simplate CEc™.

Sample inoculum is pre-calculated based on the maximum absorbing rate (saturation point) of a reagent island and the total number of reagent islands on a device. When the pre-determined amount of liquid sample (i.e. water, milk, juice and food homogenous) is inoculated on to this device, each reagent island absorbs the same amount of sample. Sample can be distributed to each reagent island by simply moving the device in back-forth or circular motion. The area between each reagent island is hydrophobic and when each reagent island absorbs sample to its saturation point, there will be no sample left between the reagent islands and cross contamination between reagent island will be prevented. Liquid sample absorbed by the reagent islands also re-hydrolyzes the reagent in the reagent islands to support the growth of microorganisms in the sample.

After incubating the sample-containing device at a pre-determined temperature, reagent islands containing target microorganisms from the sample will have a change in color and/or emit fluorescent signals (positive); reagent islands lacking target microorganisms from the sample will exhibit no color change and emit no fluorescent signals (a negative result). Target microorganism concentration in the sample under testing can be calculated based on the number of positive and negative reagent islands observed using the Most Probable Numbers (MPN) method.

Figure 8:
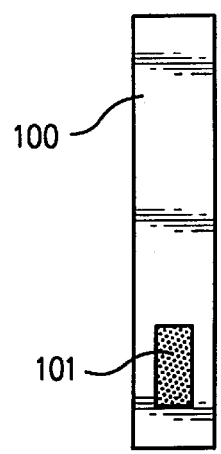
FIG. 8 is a plan view of a third embodiment of the present invention employable as a single assay dip stick device.
Figure 9:
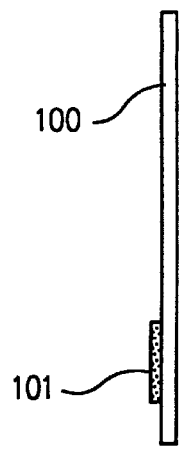
FIG. 9 is a side view of FIG. 8.

Another application of this concept is to have reagent islands lyophilized with different types of reagents. Each reagent is designed to test one specific aspect of a sample, such as microorganisms, chemicals, or any other detectable analyte of interest. Combination of these reagent islands in the same device forms a test kit providing a one-step test for multiple chemicals, analytes, or biological materials. Specifically referring to FIGS. 8 and 9, there is shown another aspect of the invention which comprises a dip stick 100 containing a reagent island 101. The stick will generally be made of plastic, but its composition is not critical and may be constructed of any hydrophobic material which will not leach into the test sample or interfere with the assay. FIGS. 8 and 9 depict the stick with a single reagent island.

Figure 10:
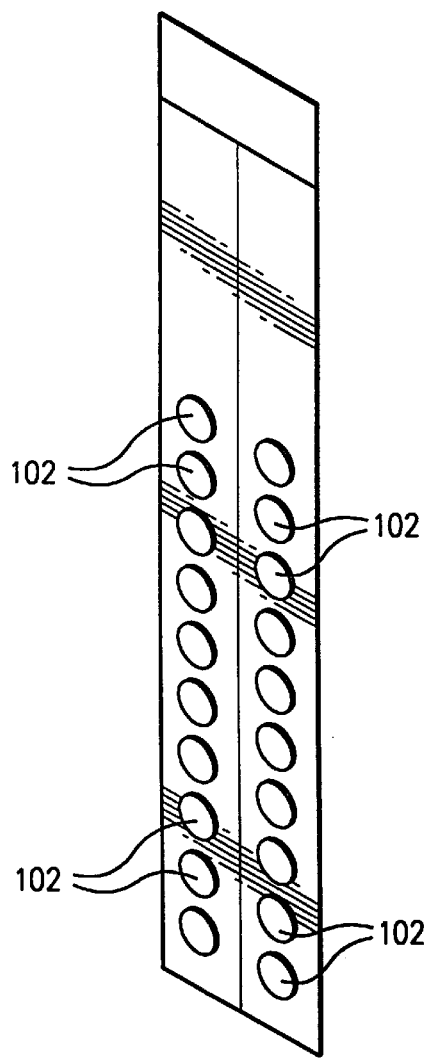
FIG. 10 is a fourth embodiment of the device of the present invention employable as dip stick assay device having a multiple reagents islands.
Figure 11:
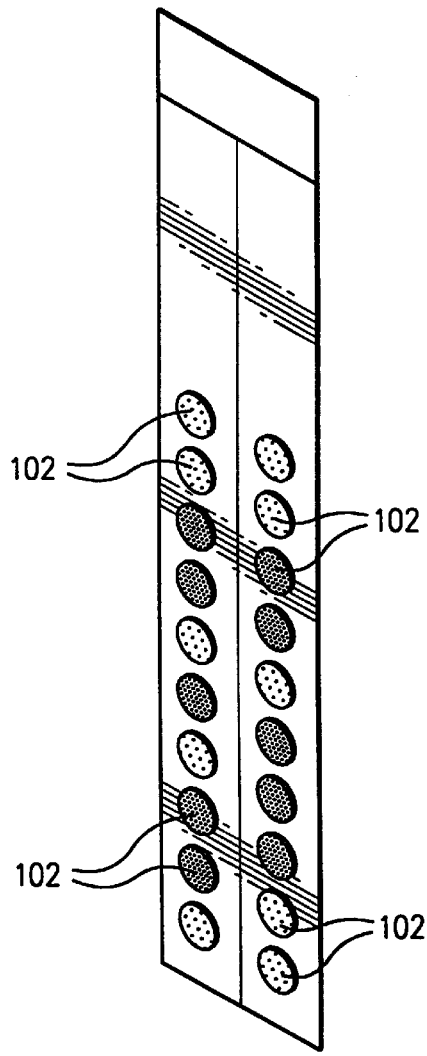
FIG. 11 shows the device of FIG. 10 in which multiple assays have been performed.

FIG. 10 depicts a preferred embodiment of the dip stick containing multiple reagent islands 102. Zones of reagent islands may be set up on the dip stick with each zone having reagent islands that contain different reagents or different combinations of reagents than the other zones, thereby enabling multiple assays to be performed on a single dip stick, each zone testing for a different analyte or microorganism. FIG. 11 depicts the dip stick assay device of FIG. 10 which has undergone the assay procedure and illustrates reagent islands showing both positive results (dark reagent islands) and negative results (white reagent islands).

Figure 12:
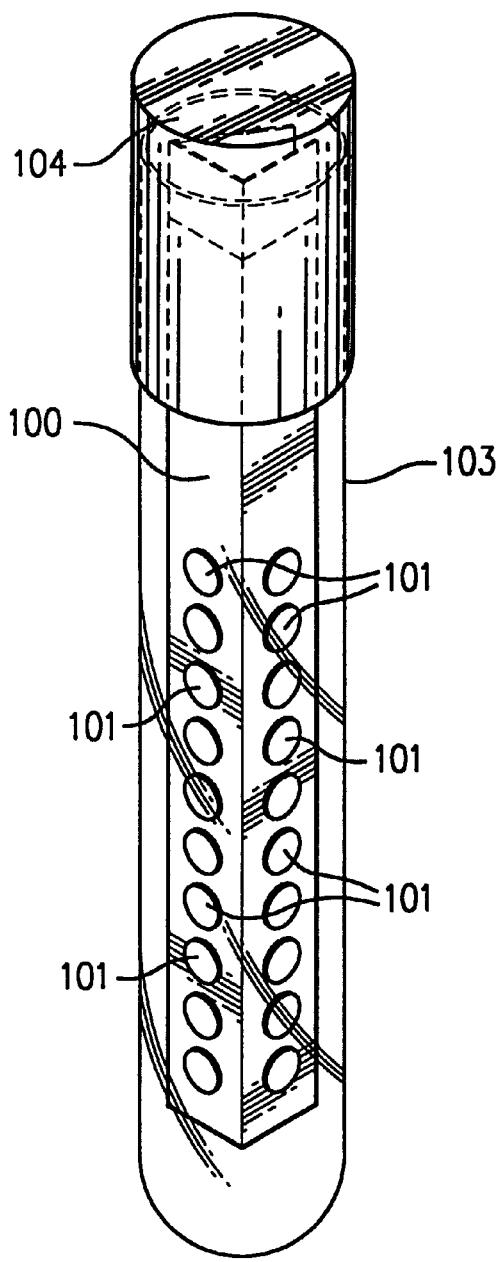
FIG. 12 is a perspective view of the fifth embodiment of the device of the present invention in which a dip stick assay device having two planes with multiple reagent islands thereon is removably insertable in a tube with a cap thereon.

FIG. 12 shows a preferred embodiment of this aspect of the invention. There is shown the dip stick 100 with multiple reagent islands 101 which is folded and inserted into a test tube 103. In this embodiment, the test tube also has a cap 104 which further protects the reagent islands from environmental factors. Of course, the device can be placed in other types of containers such as a plastic sleeve or any container which serves to protect the device. The reagent placed on the reagent island can be any reagent or combination of reagents which can be distributed onto or into the material of the reagent island.

Application of Test Sample to Dip Stick Device

The methods of applying sample to the device are varied. The dip stick can be dipped into the test sample, and left in contact long enough for the reagent islands to absorb a predetermined amount of fluid. This will generally be less than 3 seconds, but may be more depending on what material the reagent islands are constructed from. In a preferred embodiment, the reagent islands are constructed from cellulose. However, they may also be constructed of any material which is capable of absorbing and holding a volume of fluid. The test sample may also be pipetted from the test solution onto the reagent islands with a transfer pipette.

The support structure may also comprise a box made of plastic or other suitable hydrophobic material. The reagent islands may be positioned inside of the box and the box can be opened and test solution applied using a pipette or by pouring, or any suitable means. The box may have a lid to further protect the device secured thereon or as a separate piece.

Figure 13:
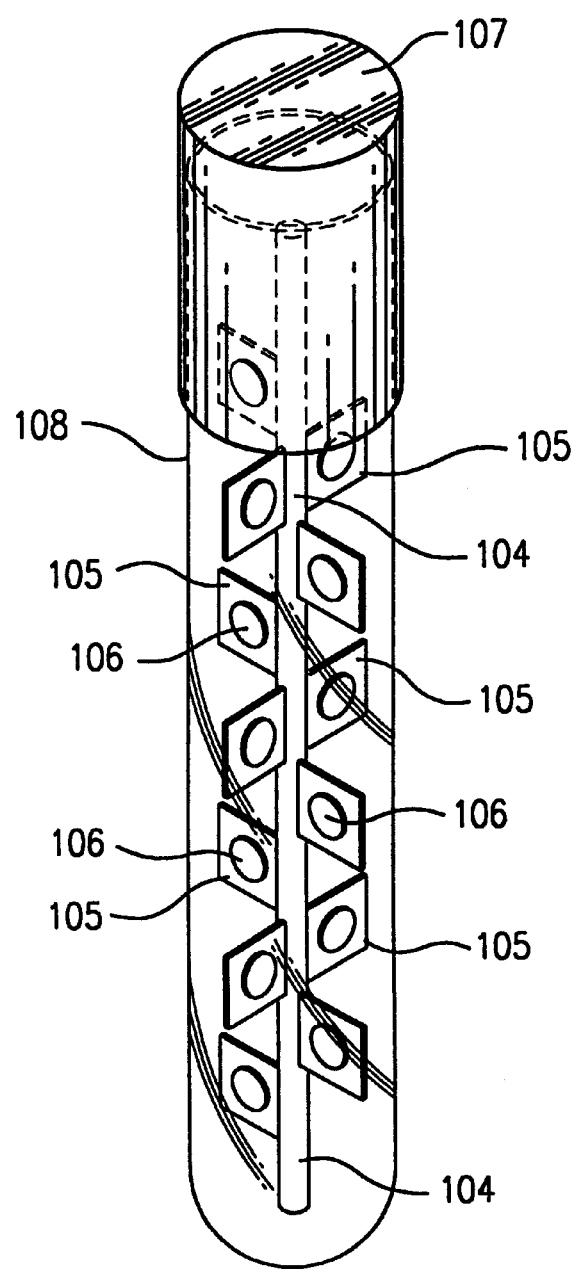
FIG. 13 is a perspective view of a sixth embodiment of the device of the present invention in which a plurality of reagent islands are located in more than one plane on a stick and are removably locatable in a tube having a removable cap thereon.

Referring now to FIG. 13, the support structure may also comprise a center support 104 to which "leaves" 105 are attached and support the reagent islands 106. The leaves can be arranged in a three-dimensional structure as depicted in FIG. 13, thereby maximizing the number of leaves which can be accommodated on one device. The device can be placed into a circular container 108 and a cap 107 placed thereon to provide further protection for the device before, during, and after development of the assay.

Pipette Device

Figure 14:
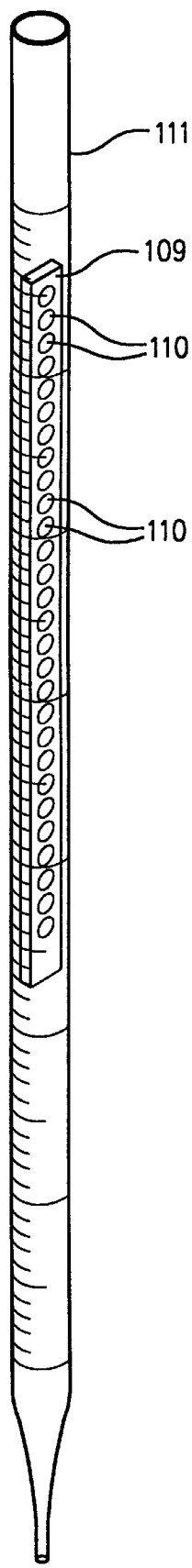
FIG. 14 is a perspective view of a seventh embodiment of the device of the present invention in which a laboratory pipette contains an elongate block having a plurality of reagent islands on one or more sides thereof.

Referring now to FIG. 14, in another aspect, the invention provides a device comprising a support structure 109 which is contained within a laboratory pipette 111. Multiple reagent islands 110 are contained on or within the support structure 109. The reagent islands are comprised of a solid absorbant material, such as cellulose, that is first cut into the desired shape and affixed to support structure 109. Preferably, the support structure 109 has more than one side with reagent islands 110 thereon. The support structure 109 is most preferably formed of a synthetic polymer, such as a plastic, and is inserted into a laboratory pipette 111 which is preferably comprised of glass or plastic and has a tapered end for sample uptake. Sample may be merely drawn into the pipette by an asperation apparatus known in the art, allowed to remain for a time sufficient for the reagent islands to absorb a predetermined volume of test sample, and expelled from the device. The device is then incubated for a time sufficient to develop the assay, and the results determined. The pipette itself comprises both a simple means of applying sample to the test device, as well as a protective function.

Example 1

A Bacterial Detection System for coliforms and *E. coli* in Milk Using the Dip Stick Device The following is an example of how the present invention provides a method of coliform detection in milk that is easy, does not comprise many steps, and provides results that are easy to interpret. The assay was conducted using a test device with multiple reagent islands, each of which absorbed 0.033 ml of milk. The milk was added to the test device and was auto-aliquoted to all the reagent islands. The sample was incubated for 24 hours and provided the number of coliforms present by examining how many of the reagent islands change color. The number of coliforms present is determined based on the MPN chart. The data obtained from the assay are set out in Table 1. The flexibility of the test device's uptake ability is emphasized since volume uptake can be easily adjusted by adjusting the number and/or sizes of the reagent islands. The device also has the capability to have multiple tests on the same device, by impregnating reagent islands with different media.

TABLE 1

| Milk Samples | Dipstick Device (cfu/ml) |
|---|---|
| #7197A | 10.3 |
| #7197B | 11.8 |
| #7197C | 16.4 |
| #710 | 56.3 |
| #713 | 18 |
| #3B1 | 0 |
| #3B2 | 37 |
| #2B2 | 0 |
| #2B1 | 9.3 |
| #618 | 69.1 |
| #618A | All + |
| #622A | 12 |
| #622B | 36 |
| #622C | 3 |
| #7697A | 56 |
| #7697B | 22 |
| #7697C | 16 |
| #7697D | 31 |
| #811 | 3 |
| #815 | 16 |
| #813 | 6.2 |
| Mean: | 23.41 |
| Std. Deviation | 20.75 |

The invention has been described in detail with particular reference to certain preferred embodiments thereof, but it will be understood that variations and modifications can be effected within the spirit and scope of the invention.

What is claimed is:

1. A device for determining the presence or amount of an analyte or microorganism in a test solution, said device comprising:
   a substantially hydrophobic support structure,
   at least one reagent island immobilized on said support structure, said at least one reagent island capable of absorbing a predetermined volume of the test solution; and,
   means for determining the presence or absence of an analyte or microorganism positioned on or within said reagent island.

2. The device of claim 1 further comprising a plurality of reagent islands immobilized on said support structure.

3. The device of claim 1, wherein said means for determining the presence or amount of an analyte or microorganism is a powder incorporated onto or within said reagent island.

4. The device of claim 1 wherein said means for determining the presence or amount of an analyte or microorganism comprises a reagent that leads to production of a sensible signal when a target analyte or microorganism is present in a sample.

5. The device of claim 1 wherein said at least one reagent island is comprised of cellulose.

6. The device of claim 1 wherein said substantially hydrophobic support structure is comprised of a plastic.

7. The device of claim 1, wherein said at least one reagent comprises cells of at least one bacterial strain.

8. The device of claim 1, further comprising a plurality of different reagents.

9. The device of claim 1, wherein said device comprises a plurality of reagent islands and said at least one reagent comprises different combinations of reagents located in different ones of said reagent islands to provide a plurality of different assays in said plate.

10. A device for determination of the presence or amount of a microorganism or an analyte in a sample, said device comprising a solid support structure comprising at least one surface, said at least one surface defining a plurality of discrete reagent islands, each of said reagent island being adapted to hold an aliquot of liquid and being sized, shaped, and formed of a material suitable to hold said aliquot within said reagent islands, at least one of said reagent islands containing at least one reagent for the detection of a microorganism or analyte such that said device will not provide a positive response for an analyte or microorganism in the absence of a microorganism or analyte present in a sample applied to said device.

11. The device of claim 10, wherein said reagent islands together take up a preselected total volume.

12. The device of claim 10, wherein said at least one reagent comprises a plurality of reagents located in separate islands.

13. The device of claim 10, wherein said reagent islands are arranged in a plurality of zones, wherein each said zone provides a separate assay.

14. The device of claim 10, wherein said reagent islands are adapted to retain aliquots of liquid sample by surface tension.

15. The device of claim 10, wherein said reagent islands are adapted to retain aliquots of liquid sample by absorption.

16. The device of claim 10, wherein said reagent islands are designed and adapted to each take up equal volumes.

17. The device of claim 10, wherein said reagent islands are located on more than one surface of said solid support structure.

18. The device of claim 10, wherein said device is a plate.

19. The device of claim 10, wherein said support structure is an elongate strip.

20. The device of claim 10, wherein said support structure is constructed of a hydrophobic material.

21. The device of claim 10, wherein said at least one reagent is selected from the group consisting of growth medium, bacterial cells, enzyme, and enzyme substrate.

22. The device of claim 21, wherein said growth medium is an indicator growth medium.

23. A method of manufacturing a device useful for detecting an analyte or microorganism in a test solution, said method comprising the steps of:

providing a material capable of absorbing a predetermined volume of liquid per amount of the material;

preparing at least one reagent island from said material;

combining said material with a means for detecting the presence or amount of an analyte or microorganism; and, securing said island to a substantially hydrophobic support structure.

24. A method of detecting the presence or amount of an analyte or microorganism in a test solution comprising the steps of:

contacting a test solution with at least one reagent island immobilized on a support structure, said at least one reagent island capable of absorbing a predetermined volume of test solution and including means for determining the presence or amount of an analyte or microorganism positioned on or within said reagent island;

separating the test solution from said reagent island immobilized on a support structure after said reagent island has absorbed a predetermined amount of test sample;

subjecting said reagent island to reaction parameters which allow development of the reagent whereby a sensible signal is provided; and determining the presence or amount of an analyte or microorganism.

25. A method for the detection of the presence or amount of an analyte or microorganism in a test solution, said method comprising the steps of:

selecting a test solution for the detection of the presence or amount of an analyte or microorganism;

providing a device comprising a substantially hydrophobic support structure and at least one reagent island immobilized on said support structure, said reagent island capable of absorbing a predetermined volume of test solution, said reagent island including means for determining the presence or amount of an analyte or microorganism;

contacting said device with a test solution for a time sufficient to allow said reagent island to absorb said predetermined volume; and, allowing said means for determining the presence or amount of an analyte or microorganism to determine the presence or amount of said analyte or microorganism.

* * * * *